US012558499B2

(12) United States Patent
Larsson et al.

(10) Patent No.: US 12,558,499 B2
(45) Date of Patent: Feb. 24, 2026

(54) BREATHING APPARATUS WITH VENTILATION STRATEGY TOOL

(71) Applicant: MAQUET CRITICAL CARE AB, Solna (SE)

(72) Inventors: Ake Larsson, Jarfalla (SE); Madlene Lahtivuori, Johanneshov (SE); Anette Sunna, Johanneshov (SE); Arne Lindy, Bromma (SE)

(73) Assignee: MAQUET CRITICAL CARE AB, Solna (SE)

( * ) Notice: Subject to any disclaimer, the term of this patent is extended or adjusted under 35 U.S.C. 154(b) by 915 days.

(21) Appl. No.: 17/733,433

(22) Filed: Apr. 29, 2022

(65) Prior Publication Data

US 2022/0339376 A1     Oct. 27, 2022

Related U.S. Application Data

(63) Continuation of application No. 14/768,113, filed as application No. PCT/EP2013/053073 on Feb. 15, 2013, now abandoned.

(51) Int. Cl.
A61M 16/00          (2006.01)
G06T 13/00          (2011.01)
                        (Continued)

(52) U.S. Cl.
CPC .... A61M 16/0003 (2014.02); A61M 16/0051 (2013.01); A61M 16/021 (2017.08);
                        (Continued)

(58) Field of Classification Search
CPC .......... A61M 16/0003; A61M 16/0051; A61M 16/021; A61M 2205/502; G06T 13/00
See application file for complete search history.

(56) References Cited

U.S. PATENT DOCUMENTS

| | | | |
|---|---|---|---|
| 5,333,106 A | 7/1994 | Lanpher et al. | |
| 5,769,082 A | 6/1998 | Perel | |

(Continued)

FOREIGN PATENT DOCUMENTS

| | | |
|---|---|---|
| EP | 0982043 A2 | 3/2002 |
| JP | 2000070370 A | 3/2000 |

(Continued)

OTHER PUBLICATIONS

Respiratory Airflow and Volume ADI Instruments, 2005, 1-16.

(Continued)

*Primary Examiner* — Margaret M Luarca
(74) *Attorney, Agent, or Firm* — McCoy Russell LLP

(57)          ABSTRACT

A system includes a breathing apparatus, a display unit and a processing unit that is operatively connected to the display unit. The processing unit is configured to provide a graphical visualization on the display unit. The graphical visualization in turn includes a combination of a target indication for at least one ventilation related parameter of a ventilation strategy for a patient ventilated by the apparatus, and a reciprocating animation of the at least one ventilation related parameter relative the target indication. The target indication is for instance based on input of a user, such as an operator of the breathing apparatus. Alternatively, or in addition, it may be a default value stored on a memory unit being operatively connected to the processing unit. Alternatively, or in addition, the target indication is based on a measurement value of said patient's physiology or anatomy. In this manner, the system informs clinicians in a clear and easily understandable way how a current patient ventilation is related to a chosen ventilation strategy.

17 Claims, 8 Drawing Sheets

(51) Int. Cl.
| | |
|---|---|
| *G09B 23/28* | (2006.01) |
| *G16H 40/63* | (2018.01) |
| *G16Z 99/00* | (2019.01) |

(52) U.S. Cl.
CPC ............ *G06T 13/00* (2013.01); *G09B 23/288* (2013.01); *G16H 40/63* (2018.01); *G16Z 99/00* (2019.02); *A61M 2205/502* (2013.01); *A61M 2230/40* (2013.01)

(56) References Cited

U.S. PATENT DOCUMENTS

| | | | |
|---|---|---|---|
| 6,099,481 | A | 8/2000 | Daniels et al. |
| 6,679,258 | B1 | 1/2004 | Strom |
| 2002/0015034 | A1 | 2/2002 | Malmborg |
| 2004/0074495 | A1 | 4/2004 | Wickham et al. |
| 2009/0024008 | A1 | 1/2009 | Brunner et al. |
| 2010/0030293 | A1 | 2/2010 | Sarkar et al. |
| 2011/0087117 | A1 | 4/2011 | Tremper et al. |
| 2011/0259333 | A1 | 10/2011 | Sanchez et al. |
| 2012/0180793 | A1 | 7/2012 | Schoepke |
| 2012/0185792 | A1 | 7/2012 | Kimm et al. |
| 2012/0226444 | A1* | 9/2012 | Milne ............... A61M 16/0051 702/19 |
| 2012/0291784 | A1 | 11/2012 | Robinson et al. |
| 2013/0125883 | A1* | 5/2013 | Bonassa .............. A61M 16/024 128/204.23 |
| 2013/0150734 | A1 | 6/2013 | Orr et al. |
| 2013/0245481 | A1 | 9/2013 | Tremper |

FOREIGN PATENT DOCUMENTS

| | | | |
|---|---|---|---|
| JP | 2002153429 | A | 5/2002 |
| WO | 2006127573 | A2 | 11/2006 |
| WO | 2007085109 | A1 | 8/2007 |
| WO | 2012029034 | A1 | 3/2012 |
| WO | 2012083276 | A1 | 6/2012 |

OTHER PUBLICATIONS

Mann, Fred, Basics of Mechanical Ventilation, Sep. 25, 2013, 1-13.
Cvach, Maria M., et al. Ventilator Alarms in Intensive Care Units: Frequency, Duration, Priority, and Relationship to Ventilator Parameters, International Anesthesia Research Society, 2018, 1-4.
Liu, Yuanhua et al., Usability Evaluation of a GUI Prototype for a Ventilator Machine, Journal of Clinical Monitoring and Computing, 2004, 365-372, vol. 18, Nos. 5-6.
ResMed Atral Series User Guide, ResMed Ltd., 2014, 79 pages.
Bar Graphs—webpage from https://web/mit.edu/course/21/21.guide/graf-bar.htm (downloaded Apr. 6, 2020). 2 pages.
Plot Cartesian Coordinate Points on a Cartesian Graph, at https://www.dummies.com/education/math/pre-algebra/plot-cartesian-coordinate-points-on-a-cartesian-graph/ (downloades Apr. 6, 2020). 14 pages.
English Translation of Japanese Office Action Notice of Reasons for Rejection issued Nov. 11, 2019 during the prosecution of corresponding Japanese Patent Application No. 2018-223422, 6 pages.
Erkadi, Ventilation, Jan. 19, 2013, erkadi.com.
Extended European Search Report issued Jun. 14, 2022 during the prosecution of corresponding European Patent Application No. 22151740.0, 9 pages.

* cited by examiner

BREATHING APPARATUS WITH VENTILATION STRATEGY TOOL

CROSS REFERENCE TO RELATED APPLICATIONS

This patent application is a continuation application of U.S. patent application Ser. No. 14/768,113, filed on Aug. 14, 2015, which is the national stage application of International Stage Patent Application PCT/EP2013/053073, filed Feb. 15, 2013, the disclosures of which are incorporated herein by reference in their entireties.

BACKGROUND OF THE INVENTION

Field of the Invention

This invention pertains in general to the field of breathing systems for ventilating patients, the systems including apparatuses having a display for providing graphical user interfaces (GUI's).

Description of Prior Art

During ventilation of a patient clinicians often seek to maintain a certain ventilation strategy for a treatment which is believed particularly advantageous for a ventilated patient.

However, there is hitherto no flexible tool to provide clinicians with a status of an on-going ventilation in a clear and easily understandable way when it comes to the crucial point of how the current patient ventilation is related to a chosen ventilation strategy.

Such a tool would in particular be desired to be adaptable to the status an on-going ventilation of a patient during the ventilation itself. Also, it would be desired if the tool provided a feedback to the clinician that can be understood from a distance from a breathing apparatus. It would be desired for instance to provide a quick overview of a current ventilation strategy to the clinical user. Each ventilation strategy has a target. A quick identification of compliance of an ongoing ventilation with this target to the clinical user would be desired and allow for faster clinical decision taking related to the ventilation strategy. For instance, a patient in an isolation room or during an x-ray examination might not be approached by the clinician with undue burden.

Thus, such a tool would be advantageous if it provided the clinician with a current status of a ventilation in relation to a desired strategy, even from a distance of a breathing apparatus.

For instance for education of clinicians, it would be advantageous if this tool was provideable without a patient connected to the breathing apparatus, e.g. in a simulated ventilation. This is for instance not achieved by an animated pair of lungs moving synchronized with a breathing pattern as it only visualizes an ongoing ventilation by animating inspiration and expiration phases, but no information is provided by the animation which is related to the clinical status of the ventilation. If a ventilation strategy is changed by a clinical user, these animations remain unchanged. Further, these animations are identical for different patients and do not take into consideration any individual characteristics of specific patients and their influence on a ventilation strategy.

Hence, there is a need for such a tool implemented in a system including a breathing apparatus that can provide the ventilation, and based on adjustments thereof pursues the desired ventilation strategy. Clinical decisions related to the treatment of a ventilated patient might then be facilitated. Treatment of the ventilated patient may be improved. Cost of care can potentially reduced by the more effective treatment that can be provided when considering such a clear and easily understandable way how the current patient ventilation is related to the chosen strategy.

Thus, an improved breathing system for providing a clear and easily understandable feedback for an on-going ventilation strategy in relation to a desired outcome thereof would be advantageous.

This need is addressed by the solution according to the current disclosure.

SUMMARY OF THE INVENTION

Accordingly, embodiments of the present disclosure preferably seek to mitigate, alleviate or eliminate one or more deficiencies, disadvantages or issues in the art, such as the above-identified, singly or in any combination by providing systems, methods, etc., according to the appended patent claims.

According to an aspect of the disclosure, a system is provided. The system includes a breathing apparatus, a display unit and a processing unit that is operatively connected to the display unit, the processing unit being configured to provide on the display unit a graphical visualization including a combination of:

a target indication for at least one ventilation related parameter of a ventilation strategy for a patient ventilated by the apparatus, said target indication preferably being based on user input, such as of an operator of said breathing apparatus, a measurement value of said patient's physiology or anatomy, or a default value stored on a memory unit being operatively connected to said processing unit, and a reciprocating animation of the at least one ventilation related parameter relative the target indication.

This provides for clinicians accessing in a clear and easily comprehensible way how the current patient ventilation is related to the chosen strategy.

The ventilation strategy may include one or more ventilation related parameters desired to obtain a certain value for the specific patient, which is believed to be of particular value for the patient's treatment. Ventilation related parameter might be a desired ventilation per patient body weight, i.e. a tidal volume per kg body weight [mL/kg Ideal Body Weight] and/or a certain airway pressure. Other ventilation related parameters of such ventilation strategies are for instance the inspiratory oxygen concentration, the positive end expiratory pressure (PEEP), that are desired to obtain certain values during ventilation to pursue the ventilation strategy.

Another ventilatory parameter desired to obtain a certain value for the specific patient within a desired ventilation strategy is based on Inspired O2 (FiO2) and PEEP. A ratio of FiO2 to PEEP may be a suitable clinical parameter for a desired ventilation strategy. Suitable values for the ratio may be selected by the clinician or from a default value. The default value may for instance be based on input of a target FiO2 or target PEEP only, whereupon the processing unit automatically calculates a desired ratio. Alternatively, or in addition, the two parameters may be provided with their current values and individual targets, respectively, in graphical visualizations aggregates comprising multiple graphical visualizations as will be elucidated in the detailed description.

Input of patient length and body weight may gives a default target indication value, e.g. a Vt for a certain patient length and body weight.

The graphical visualizations of the disclosure are visualizations of a ventilatory strategy. It should be noted that the visualizations are particularly advantageous in many clinical applications.

For instance, it may be of particularly considerable value when the ventilatory strategy is affected by ventilatory parameters that are not directly linked to each other.

An example is when during Pressure Support Mode or Pressure Control Mode of a breathing apparatus a ventilatory strategy related to tidal volumes, as in some examples described below, is desired, adjustments of ventilatory parameters of the breathing apparatus are only related to ventilatory pressures, but no adjustment of a volume to be delivered to the patient is possible. The tidal volume delivered to the patient will result depending on the patient's anatomy, the tubing used, etc. The graphical visualizations as disclosed herein provide for an advantageous, immediate feedback to the clinical user of which volume is delivered to the patient in relation to a desired volume to be delivered. Any deviations may quickly be corrected by adjusting ventilatory parameters other than the ventilatory parameters of the desired strategy. In the example, target pressures may be adjusted accordingly by the clinical user such that a desired target ventilation per patient body weight, i.e. a tidal volume per kg body weight [mL/kg Ideal Body Weight], of the ventilatory strategy is obtained upon the adjustment made. It should be noted that no target volume can be directly set by the clinical user for operating the breathing apparatus during Pressure Support Mode or Pressure Control Mode.

Another example where the graphical visualizations of the disclosure are of particularly considerable value is a Volume controlled breathing mode. Here, the clinical user may adjust volume related targets in the breathing apparatus, like a minute volume of breathing gas to be delivered to the patient. However, it may as part of a ventilation strategy be desired to keep patient pressures within certain ranges, below certain threshold values, etc. As pressures are resulting from the volume related adjustments and targets for the pressures may not be entered in these ventilation modes, the graphical visualizations of the disclosure provide a particularly advantageous tool for the clinical user. Again, any deviations from target pressures of a ventilation strategy may quickly be corrected by adjusting ventilatory parameters other than the ventilatory parameters of the desired strategy. In the example, target minute volumes may be adjusted accordingly by the clinical user such that a desired target pressure of the ventilatory strategy is obtained.

Another example where the graphical visualizations of the disclosure are of particularly considerable value is a spontaneous breathing patient in a Volume Support breathing mode. In this mode, a target of a ventilation strategy may be to provide a desired minute volume to the patient. Again, any deviations from target minute volume of such a ventilation strategy may quickly be corrected by adjusting ventilatory parameters other than the ventilatory parameters of the desired strategy. In the example, Oxygen contents of the inspiratory breathing gas may be increased, the breathing mode may be changed to a mechanical (non-spontaneous) ventilation mode, etc. The clinical user is provided with a useful tool providing support for taking clinical decisions related to the treatment of the patient such that a treatment is obtained by following a desired ventilation strategy.

The reciprocating animation of the at least one ventilation related parameter relative the target indication described herein for aspects of the disclosure, and of which examples are given in the detailed description below may take various forms. It represents a current value of the parameter. During a simulation, without connected patient, it may be a simulated value thereof.

One form is a continuous form of the animation. For instance in examples having a bar graph, the movement of the front of the bar may be continuously. Continuous movement may be synchronized with the breathing cycle. The movement may for instance be forwardly (e.g. for a bar) or outwardly (e.g. for a sphere) during inspiration and vice versa during expiration, turning at a top value apex. Continuous movement may be provided in real time, based on measured values, for instance in case the values are provideable continuously. In case the values are only provideable intermittently, an averaging may be done to provide a continuous form of the animation. The movement is relative the target indication.

Alternatively movement of the ventilation strategy indicator may be non-continuously, such as stepwise. This movement may for instance be provided when the values for the parameter are updated or provided intermittently. Then the animation may be provided stepwise.

The animation is in all cases moving towards an end value of the reciprocating animation. It may be not important in which fashion the animation reaches this end value (or top value). However, the motion may provide useful information to the clinical user, e.g. its acceleration. The end value provides very useful information to the clinical user as it indicates the relation to the target value of the ventilator strategy.

According to another aspect of the disclosure, a decision support system is provided. The decision support system includes a breathing apparatus, a display unit and a processing unit being operatively connected to the display unit. The processing unit is configured to provide on the display unit a graphical visualization. The graphical visualization includes a combination of:

a target indication for at least one ventilation related parameter of a ventilation strategy for a patient ventilated by the apparatus, said target indication preferably being based on user input, such as of an operator of said breathing apparatus, a measurement value of said patient's physiology or anatomy, or a default value stored on a memory unit being operatively connected to said processing unit, and a reciprocating animation of the at least one ventilation related parameter relative the target indication.

Moreover, the graphical visualization facilitates the operator to take decisions related to adjustments of ventilatory settings of the breathing apparatus to pursue the ventilation strategy.

According to a further aspect of the disclosure, a computer-readable medium having embodied thereon a computer program for processing by a processing unit is provided. The processing unit is comprised in a breathing system including a breathing apparatus, and a display unit. The processing unit is operatively connected to the display unit, wherein the processing unit is configured to provide a graphical visualization on the display unit. The computer program comprises code segments for providing the graphical visualization including a combination of a target indication for at least one ventilation related parameter of a ventilation strategy for a patient ventilated by the apparatus, said target indication preferably being based on user input, such as of an operator of said breathing apparatus, a measurement value of said patient's physiology or anatomy, or a default value stored on a memory unit being operatively connected to said processing unit, and a reciprocating animation of the at least one ventilation related parameter relative the target indication.

According to yet a further aspect of the disclosure, a graphical user interface is provided for a breathing system. The system includes a breathing apparatus, a display unit and a processing unit operatively connected to the display unit. The processing unit is configured to provide a graphical visualization on the display unit. The graphical visualization in turn includes a combination of a target indication for at least one ventilation related parameter of a ventilation strategy for a patient ventilated by the apparatus, and a reciprocating animation of the at least one ventilation related parameter relative the target indication.

The target indication is for instance based on input of a user, such as an operator of the breathing apparatus.

Alternatively, or in addition, it may be a default value stored on a memory unit being operatively connected to the processing unit.

Alternatively, or in addition, the target indication is based on a measurement value of said patient's physiology or anatomy. Measurement values may for instance include blood gas values, measured lung time constants, brain signals, nerve signals, such as of the vagus nerve stimulating the diaphragm of the patient, etc.

Alternatively, or in addition, user input may be made by a separate input device, such as a personal communication device, communicating with the breathing apparatus and/or processing unit, e.g. via a wired or wireless link known in the art. In this manner, the system can inform clinicians in a clear and easily understandable way how a current patient ventilation is related to a chosen ventilation strategy.

Further embodiments of the invention are defined in the dependent claims, wherein features for the second and subsequent aspects of the invention are as for the first aspect mutatis mutandis.

The target indication may be displayed at a first position on the screen, wherein the first position is fixed during the animation.

The reciprocating animation may be in synchronism with a breathing cycle of a ventilated patient. Alternatively, the reciprocating animation may be in synchronism with the ventilation related parameter as measured for a ventilated patient. The reciprocating animation may be moving from a starting point to an end point in a to-and-fro motion relative the target indication. This provides for an indication how ventilation strategy is fulfilled using the graphic visualization in which the ventilation process during ventilation is animated. In the end-inspiratory, and/or end-expiratory moment, the animation will stop at a level that can be related to the specified strategy.

The starting point may be variable with the ventilation related parameter at a breathing cycle start time and synchronized therewith. The end point may be variable with the ventilation related parameter at an end expiratory time of the breathing cycle and synchronized therewith. This provides for a measure for the ventilation strategy without being limited to reciprocating processes directly synchronized with the breathing cycle.

The target indication may be updated at an interval during the ventilation.

This provides for instance for achieving a flexible ventilation strategy that is adaptable to a patient's treatment progress.

The graphical visualization may include a plurality of the ventilation related parameters in a combined target indication and reciprocating animation, each for different ventilation related parameters, and wherein the combined target indications and reciprocating animations are provided adjoining each other.

This provides for a comprehensive overall picture of even complex ventilation strategies.

The first and second combined target indications and reciprocating animations may be provided in different graphical layout.

This provides for a comprehensive overall picture of the ventilation strategy with nuanced details and easy access to details related to the progress of ventilation in relation to the ventilation strategy.

The reciprocating animation may comprise different layouts for top values of the ventilation related parameter larger than a first threshold larger than the target indication, or less than a second threshold less than the target indication, or lying outside of a range including the target indication.

This provides for an easily perceivable indication if the pursued ventilation strategy is exceeded, falls short, or not.

The graphical visualization may have a graphical appearance dependent on operational parameters of the breathing apparatus, including display of alarm limits, and different graphical appearances when alarm limits are exceeded, display of additional metrics of ventilation related parameters than of the reciprocating animation, such as a maximum inspiratory pressure, a Positive End-Expiratory Pressure (PEEP), an average airway pressure (Pmean) and a Plateau Pressure (PPlat).

It should be observed that alarm limit are not a ventilation strategy target. Thus, alarm limits are not a basis for the target indication and should not be confused with the latter.

The system may include a further animating for an on-going ventilation of the patient.

The processing unit of the system may be configured to receive input from an operator for selection of the ventilation related parameter of the ventilation strategy and/or for adjustment of a value for the target indication within a pre-defined range. The processing unit of the system may be configured to receive the ventilation related parameter as a default ventilation related parameter and/or the value for the target indication from a default value stored in a memory of the system accessible for the processing unit.

This provides for operational safety as access to certain adjustment can be restricted for some operators of the breathing system.

The display unit may be integrated into the breathing apparatus. It may be a separate display unit communicative with the breathing apparatus.

This provides for a flexible system with advantageous user acceptance.

The graphical visualization may be provided as a graphical decision support means for the operator to achieve the ventilation strategy.

This provides for easy identification if adjustments of ventilation settings are needed to achieve a desired ventilation strategy.

The disclosure provides for a tool that is executable without a patient connected to the breathing apparatus, e.g. in a simulated ventilation. The tool may be advantageous for instance for education of clinicians allowing them to be trained to effectively determine and clinically follow ventilation strategies to the benefit of patient treatment.

DESCRIPTION OF THE PREFERRED EMBODIMENTS

Figure 1A:
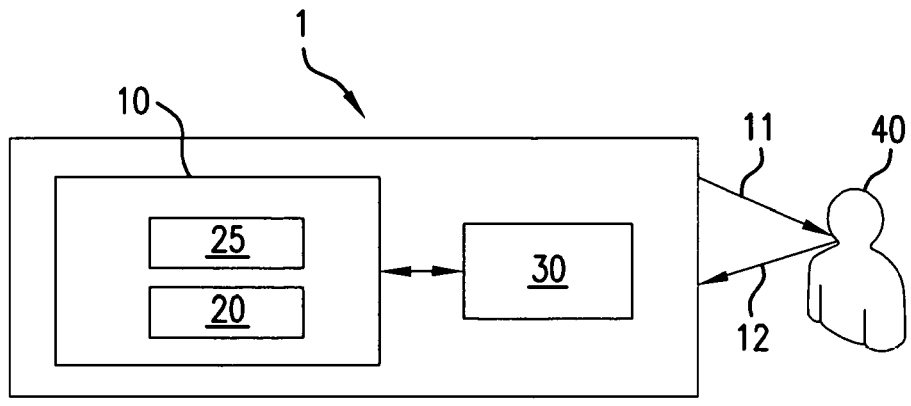
FIGS. 1A, 1B, 1C are schematic illustrations of a first, second and third system.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Figure 1B:
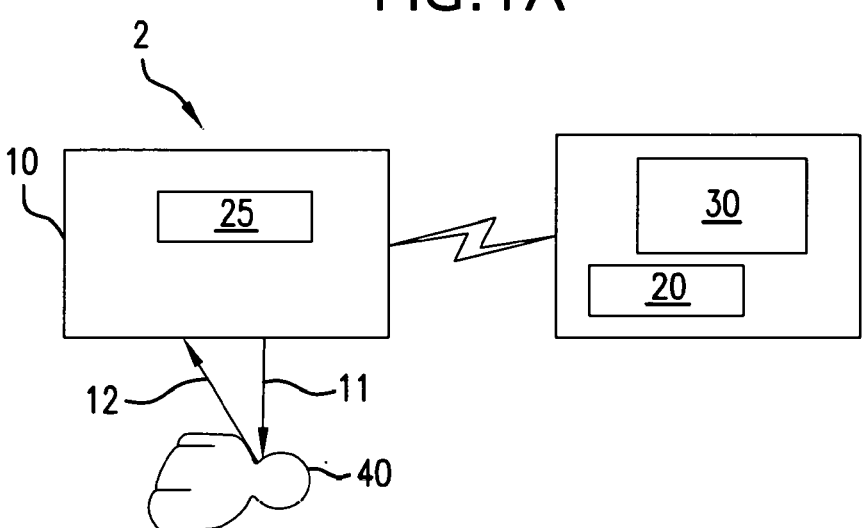
Figure 1C:
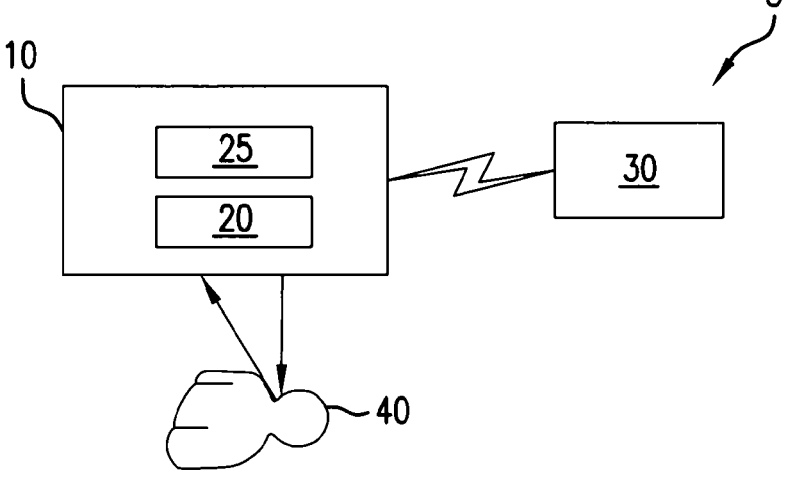

FIGS. 1A, 1B, 1C are schematic illustrations of examples of systems of the disclosure, including a first system 1, a second system 2, and a third system 3. The systems 1, 2, 3 include configurations of a breathing apparatus 10, a display unit 30 and a processing unit 20 that is operatively connected to the display unit 30. The patient 40 is fluidly connected to the system for ventilation via an inspiratory line 11 and an expiratory line 12. The processing unit 20 is configured to provide on the display unit 30 a graphical visualization. Examples for such graphical visualizations are illustrated in FIGS. 2-9 and 12, which are described in more detail below.

The graphical visualization includes a combination of at least one target indication for a ventilation strategy and a related animation of at least one current ventilation related parameter.

The target indication is either user adjusted or based on a default value. A default value for the target indication may alternatively, or in addition to operator input be based on alternative data or input sources for that value. The default target indication value may for instance be provided from an accessible database. The default value may be based on patient data, for instance based on body weight and length of a patient connected to a breathing apparatus of the system.

The default value may be included in a default range of values. The default value may be based on measured values of a patient connected to the breathing apparatus. The breathing apparatus may then provide a recommended value or a range of values from which the user can select a target value. All the aforementioned alternatives, alone or in combination, are included in the term "default" (value) for the target indication as used herein.

Examples for the ventilation related parameter include
IBW Body weight V/kg within a certain range e.g. 4-15 ml iVT/kg BW, e.g. 4, 6, 8
Ventilation related pressure parameters: PEEP, P-peak, a ratio of such parameters, such as e.g. PEEP/FiO2, and Index, etc.

In the ventilator 10 a desired ventilation strategy may for instance be specified by the user. The ventilation strategy is for example a tidal Volume in mL/predicted body weight of the patient to be ventilated. A predicted or ideal body weight can be entered directly by the clinician or calculated from patient height and gender.

During ventilation it is indicated how a ventilation strategy is fulfilled using a graphic visualization in which the ventilation process (e.g. tidal ventilation) is animated. In the end-inspiratory (or end-expiratory) moment, the animation will stop at a level that can be related to the specified strategy.

This means, if a strategy such as 6 mL/kg tidal volume per kg body weight is used and the patient is ventilated with less than 6 mL/kg tidal volume per kg body weight, the visualization will not arrive at a (fixed) graphic dividing line, the strategy target indicator. If the provided ventilation is greater than 6 mL/kg tidal volume per kg body weight, the animation will pass the graphic dividing line.

The animation is preferably paced with the respiratory rate.

The visualization can be provided as a circle, a sphere, a bar graph, a height above the horizon, a 3D object for instance expanding and collapsing, etc.

The graphical visualizations of the disclosure are visualizations only. As such, the display unit 30 does not need to be a touch sensitive. However, in certain examples the display 30 may be a touch screen providing further advantages in a suitable graphical user interface.

The animation, animated progress, or reciprocating/oscillating movement is provided for the progress over time of the ventilation related parameter. The reciprocating animation may be in synchronism with a breathing cycle of a ventilated patient. In particular, the reciprocating portion of the animation may be paced with the respiratory rate of a currently ventilated patient. Alternatively, the reciprocating animation may be in synchronism with the ventilation related parameter as measured for a ventilated patient, which may differ from the breathing cycle. The reciprocating animation may be moving from a starting point to an end point in a to-and-fro motion relative the target indication. This provides for an indication how ventilation strategy is fulfilled using the graphic visualization in which the ventilation process during ventilation is animated. In the end-inspiratory, and/or end-expiratory moment, the animation will stop at a level that can be related to the specified strategy.

The starting point may be variable with the ventilation related parameter at a breathing cycle start time and synchronized therewith. The end point may be variable with the ventilation related parameter at an end expiratory time of the breathing cycle and synchronized therewith. This provides for a measure for the ventilation strategy without being limited to reciprocating processes directly synchronized with the breathing cycle.

The reciprocating animation may comprise different layouts for top values of the ventilation related parameter larger than a first threshold larger than the target indication, or less than a second threshold less than the target indication, or lying outside of a range including the target indication.

This provides for an easily perceivable indication if the pursued ventilation strategy is exceeded, falls short, or not.

For instance, when the reciprocating animation is having a top/end value that is in a certain vicinity of the target indication, the animation may change a graphical layout to provide an easily perceivable indication. The indication may notify the user of a certain status of the patient in relation to the strategy. The status may include: within the allowable limits of the ventilation strategy, exceeding the allowable limits of the ventilation strategy, or falling short of the allowable limits of the ventilation strategy. This allows for an advantageous current status of the ventilation provided in relation to the desired ventilation strategy. The aforementioned allowable limits may be limits within a certain upper and lower threshold relative the target indication value. For instance, a threshold percentage of the target may provide the threshold/limits. An example is +/−X % of the target indication value: for too low/normal/too high. An example is +/−20%. The graphical layout change may include color changes of the graphical visualization to indicate/emphasize whether the strategy is exceeded, falls short, or not.

The graphical visualization may have a graphical appearance dependent on operational parameters of the breathing apparatus, including display of alarm limits, and different graphical appearances when alarm limits are exceeded, display of additional metrics of ventilation related parameters than of the reciprocating animation, such as a maximum inspiratory pressure, a Positive End-Expiratory Pressure (PEEP), an average airway pressure (Pmean) and a Plateau Pressure (PPlat).

A processing unit of systems as described herein may be configured to receive input from an operator for selection of the ventilation related parameter of the ventilation strategy and/or for adjustment of a value for the target indication within a pre-defined range. The processing unit of the system may be configured to receive the ventilation related parameter as a default ventilation related parameter and/or the value for the target indication from a default value stored in a memory of the system accessible for the processing unit.

This provides for operational safety, as access to certain adjustment can be restricted for some operators of the breathing system. This may be provided or administered on a care unit level in a hospital. Access to certain adjustments as input of values for the target indication, choice or selection of ventilation related parameters of desired ventilation strategies, etc., may be restricted, e.g. requiring entry of an access code.

A user definable strategy may be provided. Preferably, the strategy target(s) are adjustable by the user within certain limits for input from a default range, e.g. 4-15 ml/kg (tidal volume/body weight).

In this manner, excessive values outside of the default range are avoided, which is advantageous from a safety aspect.

The target indication may be displayed at a first position on the screen, wherein the first position is fixed during the animation.

When the first position of the target indication is at a fixed position, it may for instance be a static line, a reference line, or a reference indication other than a line.

The target indication is illustrating a desired goal or result of the ventilation strategy by means of a desired value based on one or more ventilation related parameters.

The target indication may be updated at an interval during the ventilation. This provides for instance for achieving a flexible ventilation strategy that is adaptable to a patient's treatment progress.

The ventilation strategy indicator is preferably updated with a different interval, such as every completed breath. The processing unit may suggest, provide for user confirmation, or automatically adjust the value of the target indication, e.g. when patient status changes during on-going ventilation. The target indication may be moved to a new location relative the previous value's location. Alternatively, or in addition, a numerical value displayed for or at the target indication may be updated.

During ventilation it is indicated how ventilation strategy is fulfilled using a graphic visualization in which the ventilation process (e.g. tidal ventilation) is animated. In the end-inspiratory (or end-expiratory) moment, the animation will stop at a level that can be related to the specified strategy.

This graphical visualization should not be confused with (user) adjusted ventilation parameters themselves. The graphical visualization puts the ventilation parameters values as obtained in relation to a desired ventilation strategy.

This means, if a strategy such as 6 mL/kg tidal volume per kg body weight is used and the patient is ventilated with less than 6 mL/kg tidal volume per kg body weight, the visualization will not arrive at a (fixed) graphic dividing line. If the provided ventilation is greater than 6 mL/kg tidal volume per kg body weight, the animation will pass the graphic dividing line, i.e. the target indicator 110.

In the first system 1, breathing apparatus 10, display unit 30 and processing unit 20 are integrated into a single unit. A memory unit 25 and the processing unit as well as the display 30 are for instance integrated into a single housing. The display may however be connected to a housing of a pneumatic portion (not separately illustrated) of the breathing apparatus.

The display unit 30 may be integrated into the breathing apparatus 10 as in the example of the first system 1. It may be a separate display unit communicative with the breathing apparatus. This provides for a flexible system with advantageous user acceptance.

Data for the current ventilation related parameters may be transferred from the breathing apparatus to a remote display for the graphical visualization. For instance, the display may be a bedside monitor system, such as of a patient monitor unit. The display may be a remote display, e.g. at a central nursing station. The display may be part of a portable device, such as a portable communications device. An applet on this device may provide the graphical visualization based on data received from the breathing apparatus. The processing unit may be present anywhere suitable in the system, i.e. for instance in the breathing apparatus or the display or a portable unit including the display. Data is processed by the processing unit and sent to the display unit for providing the graphical visualization thereon. Data may comprise numerical data related tot the ventilation related parameters' values, or graphical data. Sending graphical data to a display unit dispenses with the need for a processing unit at the display unit, as the numerical data is already processed by the processing unit and graphical data is thus already prepared for readily displaying the graphical visualization described herein.

In the second system 2, breathing apparatus 10 includes the memory unit. Processing unit 20 is provided at the display unit 30, which is in communication with the breathing apparatus 10. Communication may be wireless. Processing unit receives data from the breathing apparatus, which has a separate processing unit communicating with memory 25.

Other examples of systems (not shown) may have no processing unit as described herein at the display unit 30.

In the third system 3, the breathing apparatus 10 includes the processing unit 20 and memory unit 25. Display unit 30 is in communication with the breathing apparatus 10. Communication may be wireless.

Turning now to FIGS. 2-9, examples of graphical visualizations for providing feedback for a ventilation strategy related to an on-going ventilation are described. Breathing apparatus 10 is in operation ventilating the patient 40.

Figure 2:
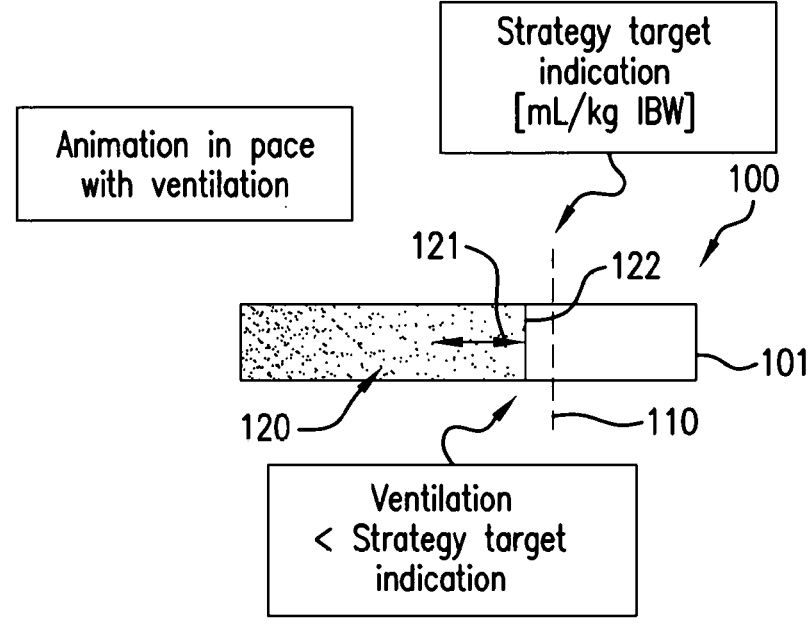
FIG. 2 is a schematic illustration of a first example of a graphical visualization in a first state.
Figure 3:
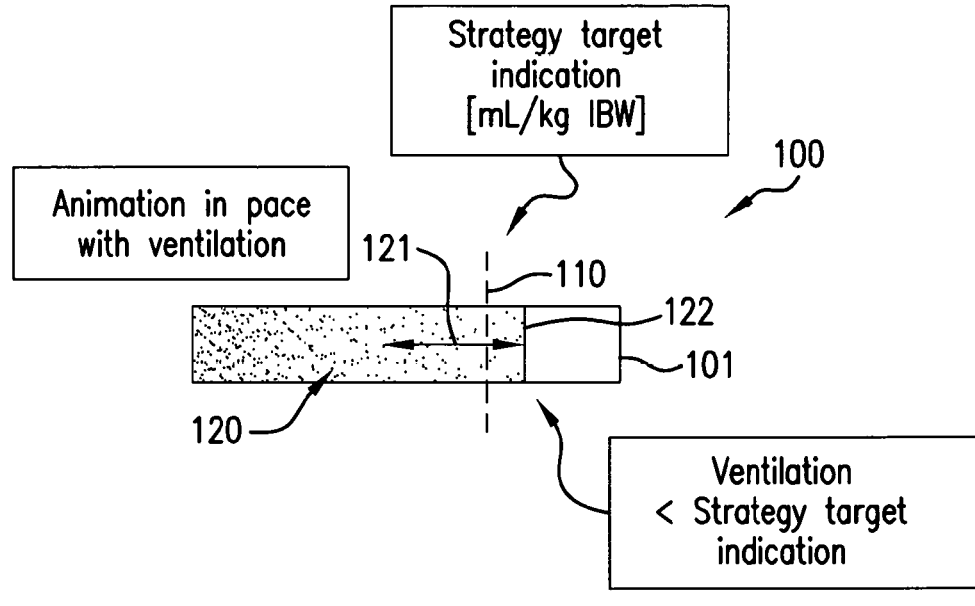
FIG. 3 is a schematic illustration of the first example of a graphical visualization in a second state.

In FIGS. 2 and 3, an example of a ventilation strategy fulfillment indicator is illustrated as a bar graph to visualize the ventilation strategy in relation to the bar graph. A graphical visualization 100 including a bar graph 101 can be seen. The graphical visualization 100 includes a target indication 110 for at least one ventilation related parameter of a ventilation strategy for a patient ventilated by the apparatus. Further, the graphical visualization 100 includes an animation 120 of the at least one ventilation related parameter relative the target indication 110. The movement of the bar is illustrated by an arrow 121. In the embodiments having a bar graph, the movement of the (front of the) bar is referred to. Movement of the ventilation strategy indicator, here in form of a bar graph may be continuously, such as reciprocating. Alternatively movement of the ventilation strategy indicator may be non-continuously, such as stepwise. The front is in this example reciprocatingly moving from the left to the right and then back. A top value 122 of the animation is reached at the point of return, or apex of the bar graph portion of the animation. The top value is in embodiments the value of interest for the clinical user. The top value may be below, on point, or exceeding the ventilation strategy target. This information of the current top value of the ventilation parameter related to the ventilation strategy in relation to the target of the ventilation allows the clinical user to take decisions for continued ventilation of the patient. Adjustments of settings of the breathing apparatus may be made when necessary.

FIG. 2 is a schematic illustration of the first example of the graphical visualization in a first state, namely when the top value 122 of the reciprocating animation is less than the value of the target indication. Here, the reciprocating animation part of the bar graph has its apex before reaching the target indication 110.

FIG. 3 is a schematic illustration of the first example of the graphical visualization in a second state, namely the top value 122 of the reciprocating animation exceeds the value of the target indication. Here, the reciprocating animation part of the bar graph has its apex after reaching the target indication 110.

In FIGS. 4-9 examples of ventilation strategy fulfillment indicators are illustrated as curved objects. The curved objects are illustrated as circular objects in the examples to visualize a ventilation strategy in relation to the curved objects, illustrated as circles. Circles are merely an example of curved objects. The object may also have other curved shapes, such as elliptical shapes, sinusoidal shapes, helical shapes, etc.

Figure 4:
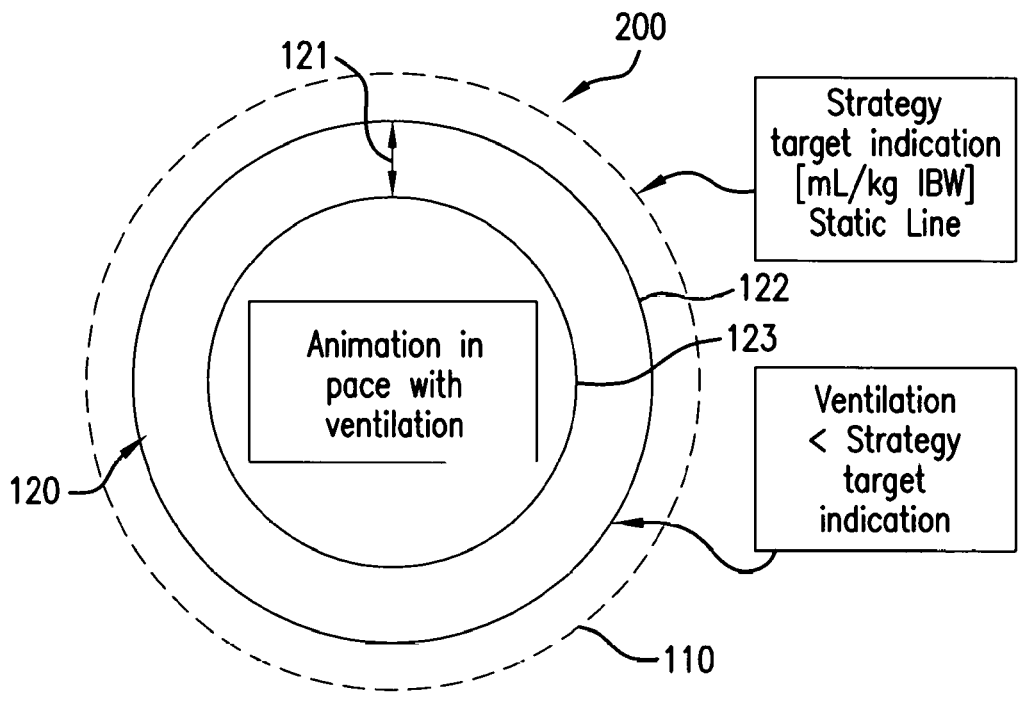
FIG. 4 is a schematic illustration of a second example of a graphical visualization in a first state.
Figure 5:
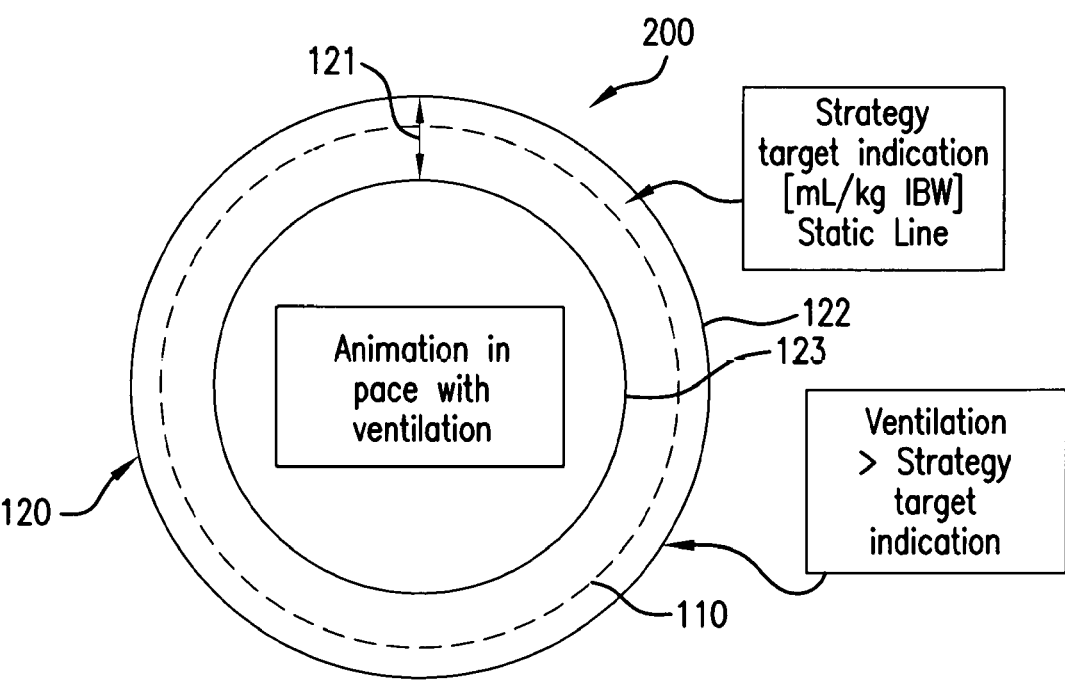
FIG. 5 is a schematic illustration of the second example of a graphical visualization in a second state.

In FIGS. 4 and 5 a further example of a ventilation strategy fulfillment indicator is illustrated as a circular object to visualize the ventilation strategy in relation to a circle.

A graphical visualization 200 including a circular object having a center can be seen. The graphical visualization 200 includes a target indication 110, here in the shape of a dotted circular line.

The ventilatory strategy target indication, here in form of a dotted line does not necessarily need to be a line, such as a dotted line, as long as it indicates the ventilation strategy target for at least one ventilation related parameter of a ventilation strategy for a patient ventilated by the apparatus. Any visual indication may be used, thicket lines, colours, shapes etc. In addition, such colour, shape etc. may change when the current ventilation is outside of the set ventilation strategy.

Further, the graphical visualization 200 includes a reciprocating animation 120 of the at least one ventilation related parameter relative the target indication 110. The reciprocating movement is illustrated by an arrow 121. The outer periphery of the filled circle is in this example reciprocatingly expanding from the center to the periphery, and then back towards the center. A top value 122 of the animation is reached at the point of return, or apex of the exemplary filled circle of the graph portion of the animation 120. The corresponding point of return of the animation at a lowest value of the ventilation related parameter is illustrated with an inner circle line 123. The values of the ventilation related parameter reciprocatingly move between the inner circle line 123 and the top value 122. It should be noted that the lower value as illustrated by circle 123 as well as the top value 122 as illustrated in the Figures are not constant values but updated based on the current values provided by the breathing apparatus 10.

The animation 120 may also be in the shape of a reciprocating 3D object. An example of such a 3D object is a sphere, or bubble.

FIG. 4 is a schematic illustration of this example of the graphical visualization in a first state, namely when the top value 122 of the reciprocating animation is less than the value of the target indication 110. Here, the reciprocating animation part of the circular object has its apex before reaching the target indication 110. FIG. 5 is a schematic illustration of this first example of the graphical visualization in a second state, namely the top value 122 of the reciprocating animation exceeds the value of the target indication 110. Here, the reciprocating animation part of the circular object has its apex beyond the target indication 110, which in this illustrated example is after reaching the target indication 110.

The graphical visualization may include multiple/a plurality of the ventilation related parameters in a combined target indication and reciprocating animation, each for different ventilation related parameters, and wherein the combined target indications and reciprocating animations are provided adjoining each other. This provides for a comprehensive overall picture of even complex ventilation strategies. Examples of such graphical visualization that include multiple ventilation related parameters and target indications related to each of the latter, are described below with reference to FIGS. 6 to 9.

Multiple visualizations provide for a comprehensive over-all picture of the ventilation strategy. Multiple combined target indications/animations for same ventilation strategy give comprehensiveness.

Multiple target indications for same ventilation related parameter might be displayed (e.g. a line for 4 ml/kg tidal volume per kg body weight and another line for 6 ml/kg tidal volume per kg body weight). Range of selectable (useful) values for target indicators may be shown as range indicators in relation to a current target indicator.

Examples for multiple ventilation related parameters include Vol+Target pressure, Vol or Pressure+Ppeak/(ml/kg).

Figure 6:
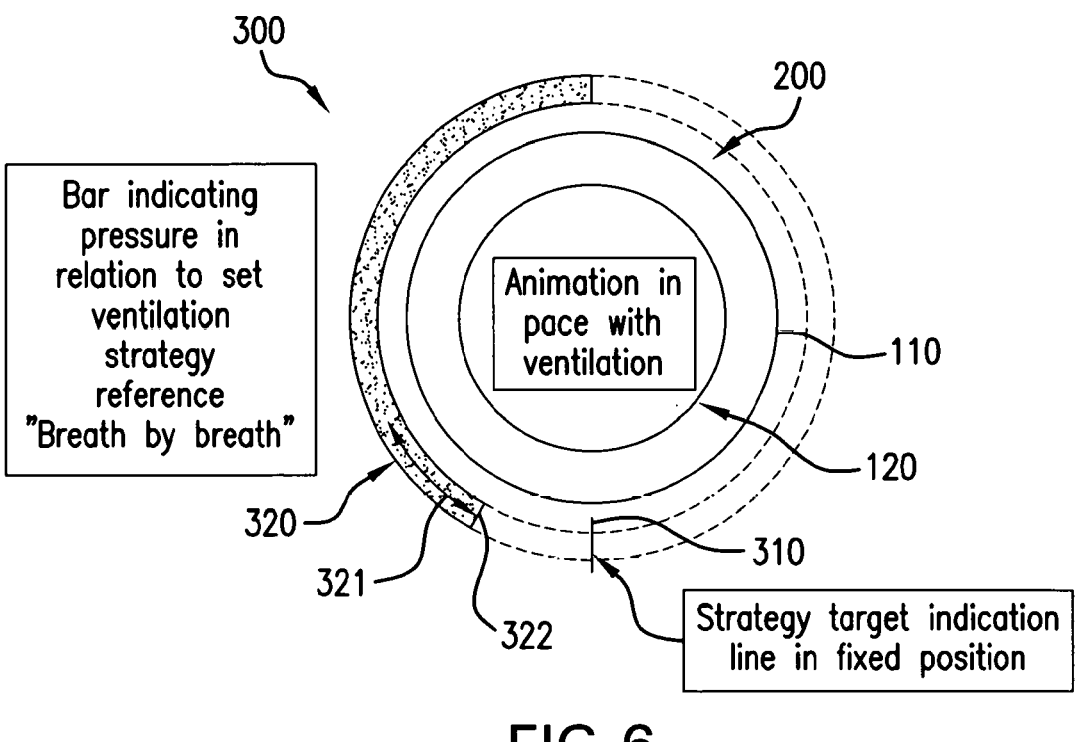
FIG. 6 is a schematic illustration of a third example of a graphical visualization in a first state.
Figure 7:
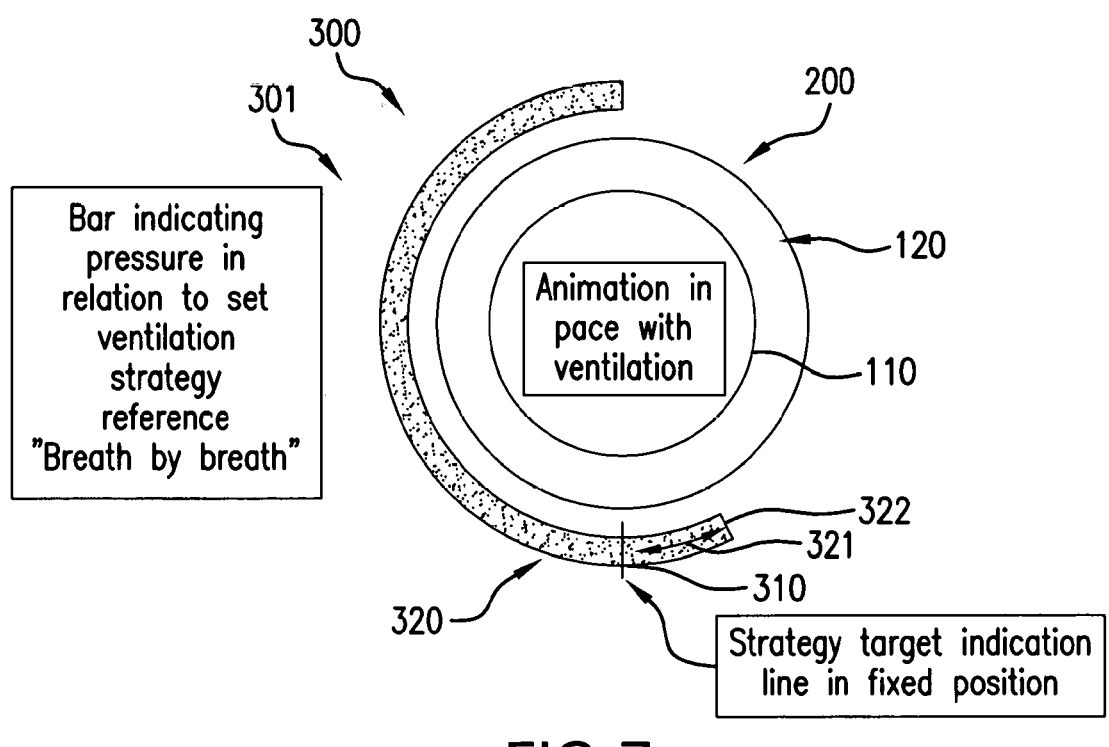
FIG. 7 is a schematic illustration of the third example of a graphical visualization in a second state.

In FIGS. 6 and 7 a further example of a ventilation strategy fulfillment indicator is illustrated. The graphical visualization includes a circular object 200 to visualize the ventilation strategy in relation to a circle, as described above with reference to FIGS. 4 and 5. The graphical visualization 200 includes a circular object having a center. The graphical visualization 200 includes a first target indication 110. In the illustration, the target indication is precisely met for the ventilation related parameter visualized by the graphical visualization 200. The graphical visualization 200 will not be described in further detail and reference is made to the above section related to FIGS. 4 and 5.

The indicator illustrated in FIGS. 6 and 7 includes a second graphical visualization 300. The second graphical visualization 300 is arranged concentric to the first graphical visualization 200. It may also be arranged non concentric in other examples. The second (or further) graphical visualization is arranged adjacent to the first (or other) graphical visualization 200 to provide an aggregate of multiple graphical visualizations for the same ventilation strategy. Each graphical visualization is related to a specific ventilation related parameter of the same ventilation strategy and has its own target indication and reciprocating animation part.

In aggregate 301, the graphical visualization 300 is pro-vided in the shape of a bent bar graph. The target indication 310 is illustrated in a 6 o'clock position, but may also be arranged at other radial positions or at other sectors than 6 o'clock. Further, the graphical visualization 300 includes a reciprocating animation 320 of the ventilation related parameter relative the target indication 310. The reciprocat-ing movement is illustrated by a double pointed arrow 321. The bent bar graph has a front with a top value 322.

The front is in this example reciprocatingly moving in a circle from a starting position, e.g. at the top of the circle, to an end position, e.g. at the bottom of the circle, and then turns back. This cycle is then repeated, wherein start and end values may be updated and changed continuously.

FIG. 6 is a schematic illustration of this example of the graphical visualization 300 in a first state, namely when the top value 322 of the reciprocating animation 320 is less than the value of the target indication 310. Here, the reciprocating animation part of the bar graph has its apex before reaching the target indication 310.

In an example, the first graphical visualization may refer to a tidal volume per kg body weight [mL/kg] and the second graphical visualization may refer to a pressure.

FIG. 7 is a schematic illustration of the example of the graphical visualization 300 in a second state, namely the top value 322 of the reciprocating animation exceeds the value of the target indication. Here, the reciprocating animation part of the bar graph has its apex after reaching the target indication 310.

The starting point of the reciprocating animation may be at a position larger than the target indication 310. In FIG. 6, a visualization of a ventilation less than the strategic target level can be seen. The animation of the first graphical visualization 200 visualizing tidal ventilation reaches out to the reference circle. However, the second graphical visual-ization 300 providing visualization of pressure levels ends below the strategic limit of the target indication 310. The breath-to-breath presentation does not reach the fixed refer-ence point, namely the target indication 310, e.g. at the 6 o'clock position.

In FIG. 7 the second graphical visualization 300 reaches and passes the reference line of the target indication 310. A visualization of pressure levels exceeding the strategic limit is given. The breath to the breath presentation reaches over the fixed reference point, namely the target indication 310.

The first and second combined target indications and reciprocating animations may be provided in different graphical layout.

This provides for a comprehensive overall picture of the ventilation strategy with nuanced details and easy access to details related to the progress of ventilation in relation to the ventilation strategy.

A comprehensive overall picture of the currently followed ventilation strategy is provided with nuanced details and easy access to detailed information related to the ventilation strategy.

In addition metrics may be displayed for the target indi-cation value.

A text may be provided for identifying the ventilation related parameter of the ventilation strategy to be followed.

Figure 8:
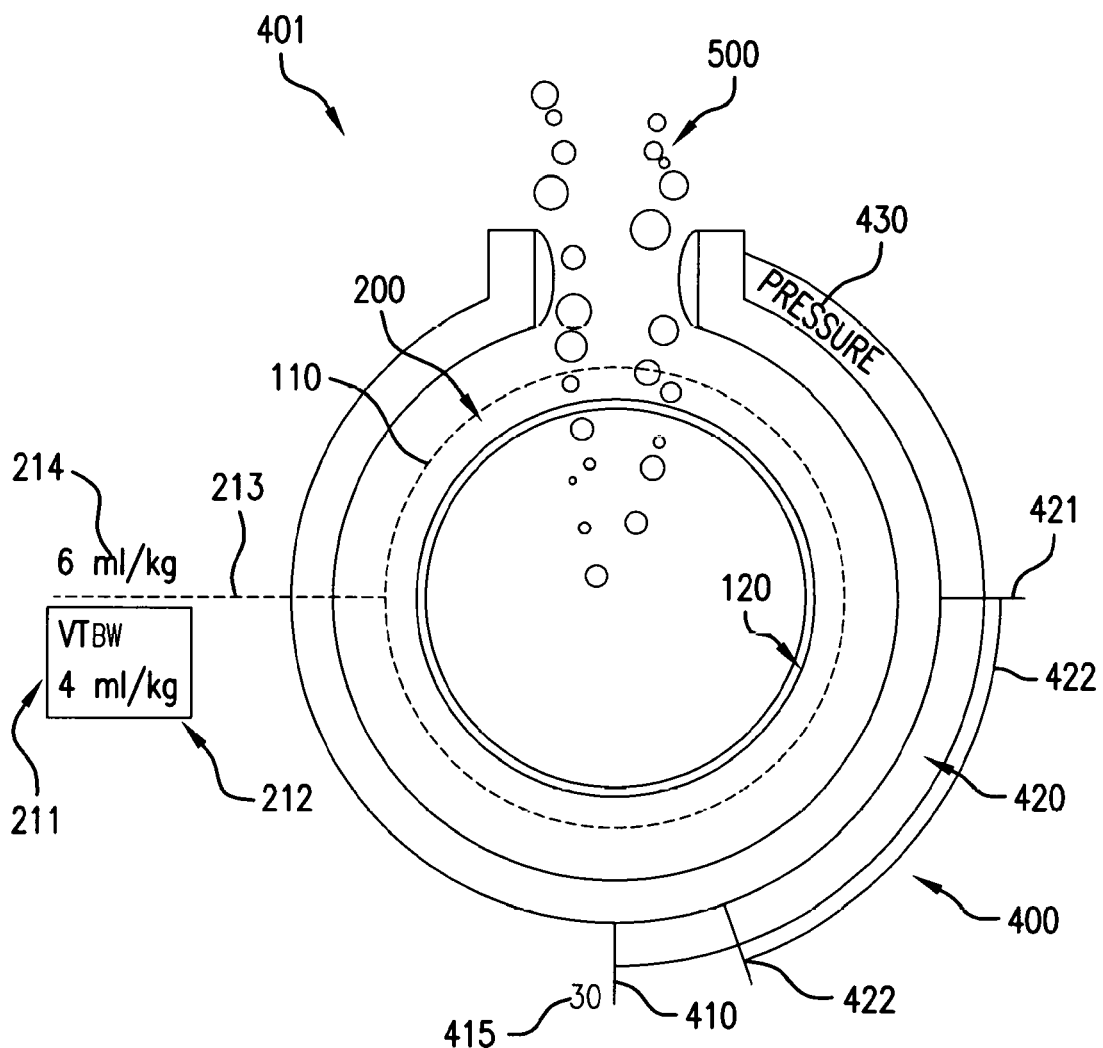
FIG. 8 is a schematic illustration of a fourth example of a graphical visualization.

FIG. 8 is a schematic illustration of another example of such a graphical visualization.

Like the aggregate 301 of graphical visualizations in FIGS. 6 and 7, the aggregate 401 illustrated in FIG. 8 includes multiple graphical visualizations and some further elements. The graphical visualization includes a circular object 200 to visualize the ventilation strategy in relation to a circle, as described above. The graphical visualization 200 includes a circular object having a center. The graphical visualization 200 includes a first target indication 110. In the illustration, the target indication is not reached by the ventilation related parameter visualized by the graphical visualization 200. The graphical visualization 200 will not be described in further detail and reference is made to the above sections.

The indicator illustrated in FIG. 8 includes a second graphical visualization 400. The second graphical visualiza-tion 400 is arranged concentric to the first graphical visu-alization 200. It may also be arranged non concentric in other examples. The second graphical visualization 400 is arranged adjacent to the first graphical visualization 200 providing an aggregate of multiple graphical visualizations for the same ventilation strategy. Each graphical visualiza-tion is related to a specific ventilation related parameter of the same ventilation strategy and has its own target indica-tion and reciprocating animation part.

The graphical visualization 400 is provided in the shape of a bent bar graph, like the second graphical visualization 300 described with reference to FIGS. 6 and 7. The graphical visualization 400 is in this example positioned to the right in the FIG. 8. A target indication 410 is illustrated in a 6 o'clock position, but may also be arranged at other radial positions or at other sectors than the 6 o'clock position. Further, the graphical visualization 400 includes a reciprocating anima-tion 420 of the ventilation related parameter relative the target indication 410. The target indication 410 is further provided with a numerical value 415 to visualize the numeri-cal value of the target indication for the specific ventilation related parameter of the graphical visualization 400. In the example, value 415 is "30". The value 415 may alternatively also be displayed together with the correct unit, here for a pressure for instance the unit [cmH2O]. The graphical visualization 400 is reciprocating between the start value indicated by a start indication 421 and the top value indicated by a top value indication 422 where the animation turns back. The range between these start and top values is illustrated by a bar 422. Bar 422 also includes a center indication.

In the example, the second graphical visualization 400 refers to a pressure. A text 430 is provided at the graphical visualization 400 for easy identification of this displayed parameter to the clinical user.

The target indication 110, in this example provided as a dotted circle, may furthermore be provided with one or more text and/or numerical objects 211. The text and/or numerical objects 211, such as the illustrated objects 212, 214 provide for a further elucidation of the current value of the target indication 110 of the current ventilation strategy. This facilitates for the clinical user to identify a current absolute value instead of a relative value only for the ventilation strategy target. A text may, like text 430, facilitate identification of the specific ventilation related parameter, or chosen values respectively default values therefor or input values for the latter. The text object 214 provides for such support of the user, which may be advantageous in particular for a decision support system. In the example, the numerical value of 6 with a corresponding unit "ml/kg", i.e. a tidal volume for a certain body weight of the ventilated patient, is provided for the ventilation strategy target. This is a value either chosen by a user, based on a measured value, provided as a default value, etc. as described above.

An indication line 213 to the target indication 110 provides the user with an easily identifiable link of the text object 213 to the target indication 213 without obstructing the animation 120.

Likewise, a text and/or numerical object may be provided as a metrics 212. In the example illustrated in FIG. 8, the metrics includes an abbreviated text VTBW for the term tidal volume (VT) per body weight (BW) allowing the user to identify the ventilation related parameter of this part of the ventilation strategy. The current value of the ventilation related parameter, here VTBW, is displayed as object 212. The current value in the example of FIG. 8, which is a still picture of an animation, is 4 ml/kg (tidal volume/body weight). The ventilation strategy target of "6 ml/kg" (text object 214 and corresponding target indication 110) is currently not reached as the current value of "4 ml/kg" fails to reach the target value. The clinical user may take suitable decisions to adapt and update the current ventilation settings so that the ventilation strategy is obtained.

A system as described herein may include a further animation for an ongoing ventilation of the patient. The further animation is advantageously integrated with or provided adjacent a graphical visualization or aggregate of multiple graphical visualization—as described herein. An example for such a further animation is for instance a plurality of bubbles 500 as illustrated in FIG. 8. The bubbles 500 are in the illustrated example provided moving back and forth. In the example, the bubbles move back and forth in relation to the center of the aggregate of graphical visualizations through an opening in circular graphical visualizations of ventilation related parameters. The further animation, such as the bubbles 500, and the motion shown therewith may be synchronized with inspiration and expiration for each direction respectively. Alternatively or in addition the further animation may provide additional information, e.g. for a leakage occurring during ventilation. A leakage may be illustrated by bubbles moving in one direction, such as outwardly in FIG. 8 without returning towards the center. Leakage illustrating bubbles may move in a different direction than the illustrated bubbles 500 in FIG. 8. In this manner, an advantageously compact visualization of multiple ventilation related parameters and the ventilation itself is provided without overloading the clinical user with information.

The animation for an ongoing ventilation of the patient, such as bubbles 500, is synchronized with the current breathing cycle of the patient. It should be noted that the periods of the reciprocating animations of the ventilation related parameters may be different than the current breathing cycle as ventilation strategies may be based on measured parameters or parameters that are not in synchronicity with the current breathing cycle. Hence, a single aggregate of graphical visualizations may have graphical visualizations oscillating at different frequencies providing the clinical user with additional information otherwise not readily available for taking decisions when updating a treatment strategy for the patient.

An example for such a parameter asynchronous with the breathing cycle is the electrical activity of the diaphragm. This may be advantageous during certain modes of ventilation. One such mode of ventilation is for instance Neurally Adjusted Ventilatory Assist (NAVA), which is a mode of ventilation that delivers ventilatory assist in proportion to and in synchrony with the patient's Edi signal, i.e. the electrical activity of the diaphragm. Edi is for instance measured using an esophageal measurement catheter. A ventilatory strategy target may be based on a desired measured Edi signal. The Edi signal may be put in relation to the tidal volume (VT). A ventilatory strategy target may be a value for Edi/VT [μV/mL]. Edi/VT may be illustrated in a way as described herein with reference to tidal volume per kg body weight. This is an example for a measurement value of said patient's physiology or anatomy mentioned above. Apart from the diphragmal EMG (Edi) other respiratory bioelectric signals and muscular signals in synchrony with breathing may be considered for the same purpose.

Another example for such a parameter asynchronous with the breathing cycle is cardiac output.

Another example for such a parameter asynchronous with the breathing cycle is the Respiratory Systolic Variation, i.e. variations in the arterial blood pressure related to breathing. Such a parameter may be provided by the Respiratory Systolic Variation Test (RSVT) as described in U.S. Pat. No. 5,769,082 of Azriel Perel, which is incorporated herein in its entirety for all purposes.

Measurement values of said patient's physiology or anatomy may thus be provided for the ventilation strategy from measurements systems external to the breathing apparatus or not directly related to patient gas measurements.

Figure 9:
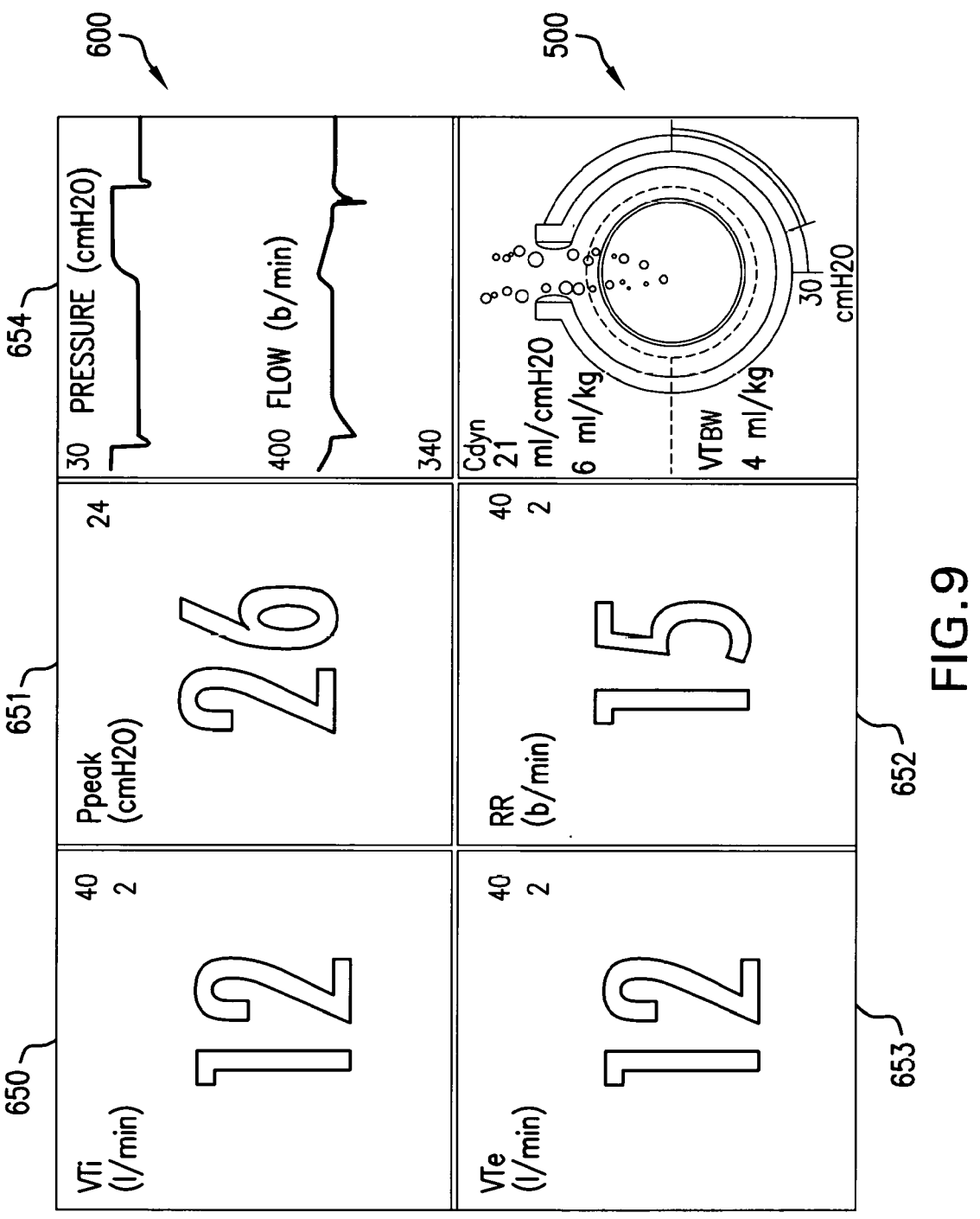
FIG. 9 is an example of a graphical user interface (GUI) including a graphical visualization as shown in FIG. 8.

FIG. 9 is an example of a graphical user interface (GUI) including a graphical visualization aggregate 500 as shown in FIG. 8. The aggregate 401 is illustrated as part of other graphical objects related to a current ventilation of a patient. Metrics objects 650, 651, 652, 653 illustrate current values of ventilatory parameters. A metrics object 650 displays a inspiratory tidal Volume VTi. A metrics object 651 displays a Peak airway pressure Ppeak. A metrics object 652 displays a Respiratory Rate RR. A metrics object 653 displays an expiratory tidal Volume VTe. A curve object 652 is for instance illustrating a pressure time curve and a flow time curve.

In examples of graphical visualizations, color changes of at least parts of aggregates described herein can be provided to indicate/emphasize whether the desired ventilation strategy is exceeded or not—as described above.

If further strategic parameters of an ongoing ventilation are to be displayed, the graphical visualization may be provided with an adapted graphical layout, such as the color or shape thereof. For instance when alarm limits are exceeded, different colors may be used than when no alarm limits are exceeded.

Other aspects of the ventilation strategy, for example, maximum pressure may be indicated in relation to the bar graph or circle as described above. This ventilation strategy indicator is preferably updated with a different interval, such as every completed breath. Other pressures can be indicated, such as Positive End-expiratory pressure, PEEP, average pressure, Pmean and Plateau Pressure, PPlat.

The graphical visualization may be provided as a graphical decision support means for the operator to achieve the ventilation strategy.

This provides for easy identification if adjustments of ventilation settings are needed to achieve a desired ventilation strategy.

If adjustments are made by a user, an easy interpreted feedback may be provided for an adjustment of the desired ventilation strategy.

Figure 10A:
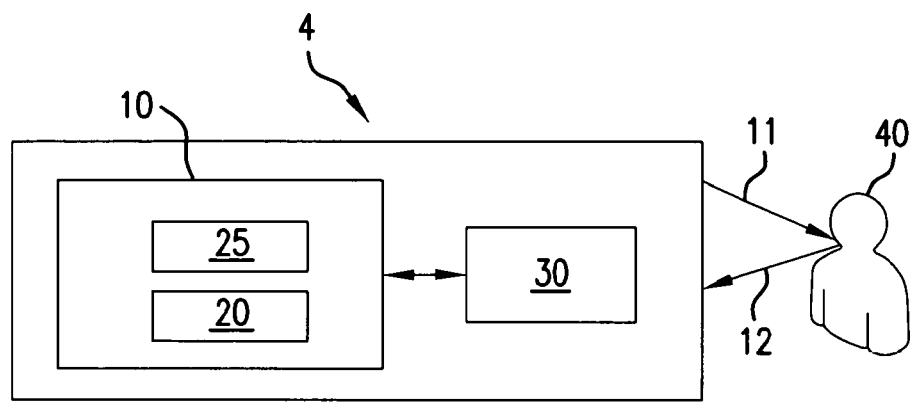
FIGS. 10A, 10B, 10C are schematic illustrations of a third, fourth, and fifth system.
Figure 10B:
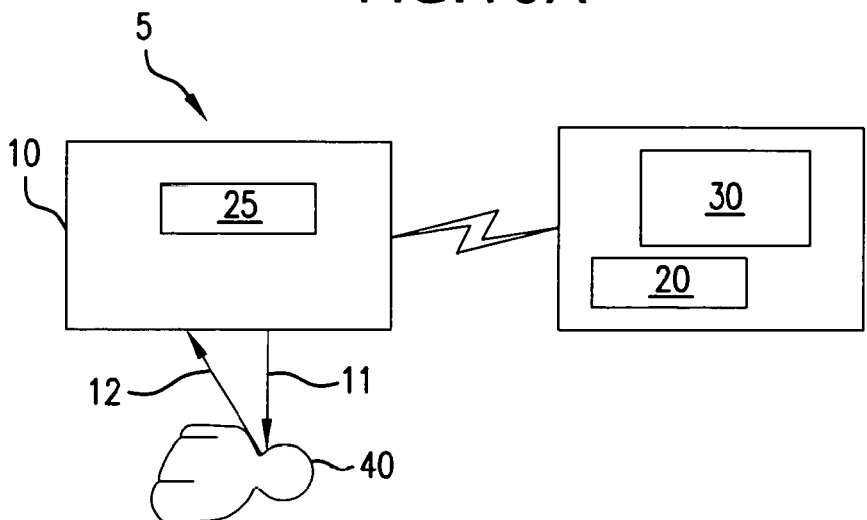
Figure 10C:
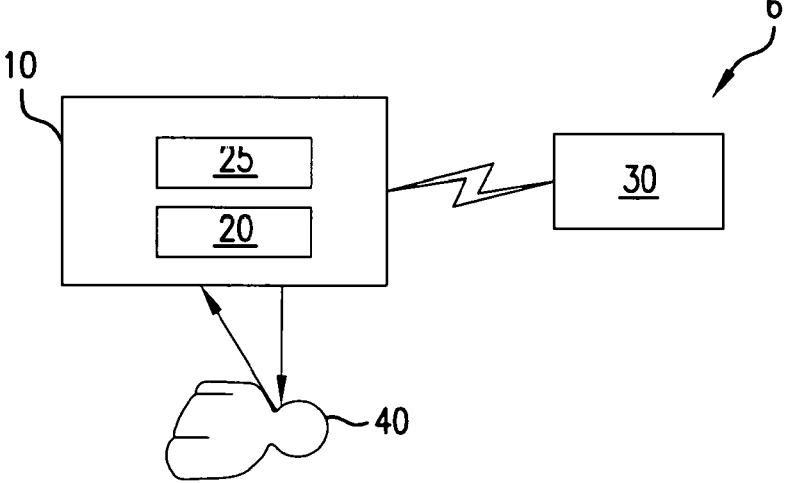

FIGS. 10A, 10B, and 10C are schematic illustrations of examples of further systems of the disclosure, including a fourth system 4, a fifth system 5, and a sixth system 6. These systems 4, 5, 6 are a decision support systems and include, like the above described systems 1,2 3 a breathing apparatus 10, a display unit 30 and a processing unit 20 operatively connected to the display unit 30. In addition to the first to third systems, the fourth to sixth systems may provide a graphical visualization facilitates the operator to take decisions related to adjustments of ventilatory settings of the breathing apparatus to pursue the ventilation strategy.

Figure 11:
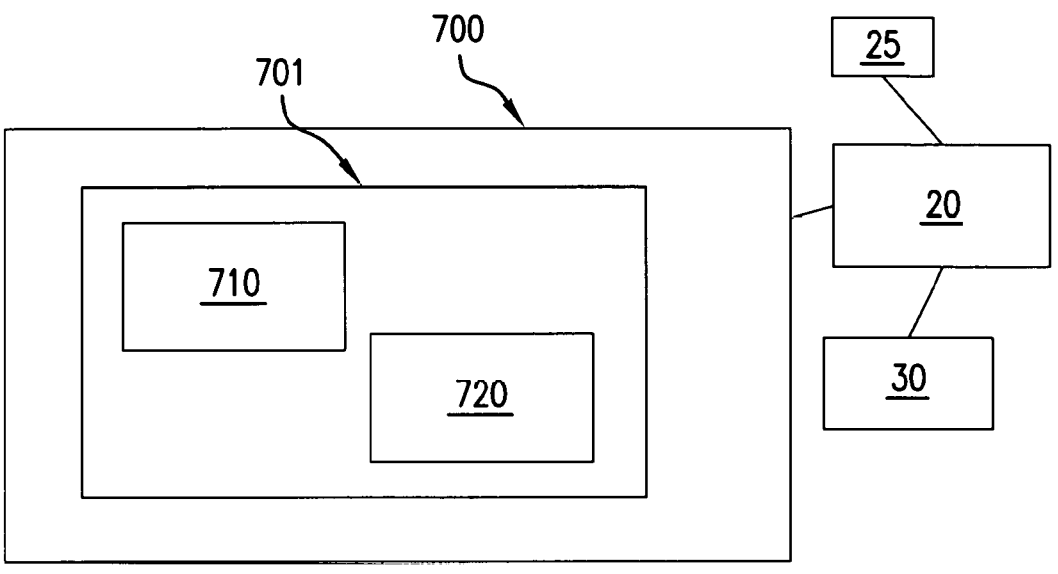
FIG. 11 is a schematic illustration of a computer-readable medium having embodied thereon a computer program for processing by a processing unit.

FIG. 11 is a schematic illustration of a computer-readable medium 700 having embodied thereon a computer program 701 for processing by a processing unit 20. The processing unit 20 is comprised in a breathing system as described above. The processing unit 20 is, as mentioned above, operatively connected to the display unit 30 providing the graphical visualization on the display unit 30. The computer program 701 comprises code segments 710, 720 for providing the graphical visualization including a first code segment 710 for providing a target indication for at least one ventilation related parameter of a ventilation strategy for a patient ventilated by the apparatus, the target indication being based for instance on input of an operator of the breathing apparatus or a default value stored on a memory unit 25 being operatively connected to the processing unit 20. Further, a second code segment 720 is provided for providing a reciprocating animation of the at least one ventilation related parameter relative the target indication in the graphical visualization.

Figure 12:
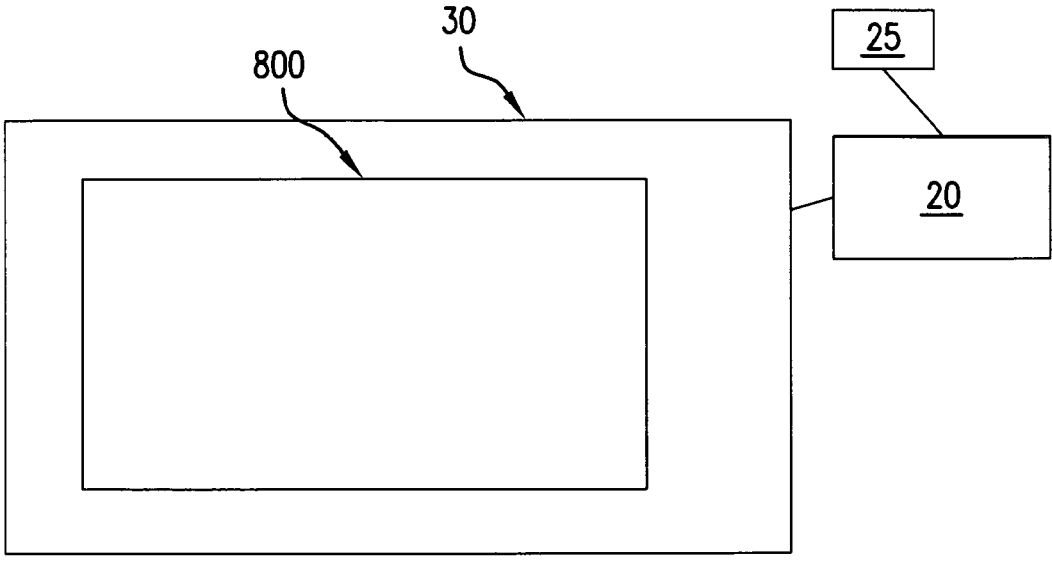
FIG. 12 is a schematic illustration of a GUI.

FIG. 12 is a schematic illustration of a graphical user interface (GUI) 800. The GUI is provided for a breathing system as described above. The graphical user interface including a graphical visualization and includes a combination of:

a target indication for at least one ventilation related parameter of a ventilation strategy for a patient ventilated by the breathing apparatus 10, the target indication being based on for instance input of an operator of the breathing apparatus 10 or a default value stored on a memory unit 25 being operatively connected to the processing unit 20, and a reciprocating animation of the at least one ventilation related parameter relative the target indication.

The present disclosure includes above specific examples. However, other embodiments than the above described are equally possible within the scope of the disclosure. Different method steps than those described above, performing the method by hardware or software, may be provided within the scope of the invention. The different features and steps of the examples may be combined in other combinations than those described. The scope of the invention is only limited by the appended patent claims.

The invention claimed is:

1. A system comprising:
   a breathing apparatus;
   a display unit and a processing unit operatively connected to said display unit;
   wherein said processing unit is configured to provide on said display unit a graphical visualization including a combination of:
   a first target indication for at least one ventilation related parameter of a ventilation strategy for a patient ventilated by said breathing apparatus, and a second target indication for a second ventilation related parameter of the ventilation strategy, wherein each of the first target indication and the second target indication is based on user input provided by an operator of said breathing apparatus, a measurement value of the patient's physiology or anatomy, or a default value stored on a memory unit that is operatively connected to said processing unit; and
   a combined reciprocating animation comprising a first reciprocating animation of the first ventilation related parameter relative to the first target indication and a second reciprocating animation of the second ventilation related parameter relative to the second target indication,
   wherein each of said reciprocating animations is in synchronism with a breathing cycle of the patient ventilated by said breathing apparatus and moves from a starting point to an end point in a to-and-fro motion relative said target indications, and wherein said end points provide an indication of whether said first and second ventilation related parameters are below, on point, or are exceeding their respective target indication,
   wherein the first and second ventilation related parameters are tidal volume per kg body weight (ml/kg) and a pressure,
   wherein the combined reciprocating animation is provided on the display unit during ventilation of the patient in a pressure support mode, a pressure control mode, a volume support mode, or a volume controlled mode.

2. The system of claim 1, wherein target pressures may be adjusted accordingly by the user in pressure support mode or pressure control mode such that a desired tidal volume of the ventilator strategy is obtained upon the adjustment made or target minute volumes may be adjusted accordingly by the user in volume controlled mode that a desired target pressure of the ventilator system is obtained.

3. The system of claim 1, wherein said target indication is displayed at a first position on a screen of said display unit, wherein said first position is fixed during said reciprocating animation.

4. The system of claim 1, wherein said target indication is updated at an interval during said ventilation.

5. The system of claim 1, wherein said first and second reciprocating animations are provided adjoining each other.

6. The system of claim 1, wherein any or both of said first and second reciprocating animations comprises a layout selected from the group consisting of: a layout for top values of said ventilation related parameter larger than a first threshold larger than said target indication, a layout for top values of said ventilation related parameter less than a second threshold less than said target indication, and a layout for top values of said ventilation related parameter lying outside of a range including said target indication.

7. The system of claim 1, wherein said graphical visualization has a graphical appearance dependent on operational parameters of said breathing apparatus, including display of alarm limits, and wherein said graphical visualization has a different graphical appearance when alarm limits or target values are exceeded than when alarm limits or target values are not exceeded, and said graphical visualization has a display of additional metrics of ventilation related parameters than of said reciprocating animation, wherein the additional metrics of ventilation related parameters are selected from the group consisting of: a maximum inspiratory pressure, a Positive End-Expiratory Pressure (PEEP), an average airway pressure (Pmean) and a Plateau Pressure (PPlat).

8. The system of claim 1, including a further animation for an ongoing respiration of said patient.

9. The system of claim 1, wherein said processing unit being configured to receive input from an operator for selection of said ventilation related parameter of said ventilation strategy and/or for adjustment of a value for said target indication within a pre-defined range; or said ventilation related parameter is a default ventilation related parameter and/or said value for said target indication is a default value stored in a memory of said system accessible for said processing unit.

10. The system of claim 1, wherein said display unit is integrated into said breathing apparatus and/or a separate display unit communicative with said breathing apparatus.

11. The system of claim 1, wherein said graphical visualization is provided as a graphical decision support means for said operator to achieve said ventilation strategy.

12. The system of claim 1, wherein said graphical visualization further includes a display of additional metrics of ventilation related parameters than of said reciprocating animation wherein the additional metrics are one or more metrics selected from the group consisting of: a maximum inspiratory pressure, a Positive End-Expiratory Pressure (PEEP), an average airway pressure (Pmean) and a Plateau Pressure (PPlat).

13. The system of claim 1, wherein the pressure is a positive end expiratory pressure or an airway pressure.

14. The system of claim 1, wherein any or both of the first and second reciprocating animations is a reciprocating bar graph or a radially reciprocating circle.

15. A decision support system comprising a breathing apparatus, a display unit and a processing unit operatively connected to said display unit, wherein said processing unit is configured to provide on said display unit a graphical visualization including a combination of:

a first target indication for at least one ventilation related parameter of a ventilation strategy for a patient ventilated by said breathing apparatus, and a second target indication for a second ventilation related parameter of the ventilation strategy, wherein each of the first target indication and the second target indication is based on user input provided by an operator of said breathing apparatus, a measurement value of the patient's physiology or anatomy, or a default value stored on a memory unit that is operatively connected to said processing unit; and a combined reciprocating animation comprising a first reciprocating animation of the first ventilation related parameter relative to the first target indication and a second reciprocating animation of the second ventilation related parameter relative to the second target indication, wherein each of said reciprocating animations is in synchronism with a breathing cycle of the patient ventilated by said breathing apparatus and moves from a starting point to an end point in a to-and-fro motion relative said target indications, and wherein said end points provide an indication of whether said first and second ventilation related parameters are below, on point, or are exceeding their respective target indication, wherein the first and second ventilation related parameters are tidal volume per kg body weight (ml/kg) and a pressure, wherein the combined reciprocating animation is provided on the display unit during ventilation of the patient in a pressure support mode, a pressure control mode, a volume support mode, or a volume controlled mode.

16. A computer-readable non-transitory, data storage medium encoded with programming instructions, wherein said data storage medium is loaded into a processor of a system comprising a breathing apparatus, and a display unit operatively connected to said processor, wherein said processor is configured to provide on said display unit a graphical visualization, and said programming instructions cause said processor to include, in said graphical visualization, a combination of:

a first target indication for at least one ventilation related parameter of a ventilation strategy for a patient ventilated by said breathing apparatus, and a second target indication for a second ventilation related parameter of the ventilation strategy, wherein each of the first target indication and the second target indication is based on user input provided by an operator of said breathing apparatus, a measurement value of the patient's physiology or anatomy, or a default value stored on a memory unit that is operatively connected to said processing unit; and a combined reciprocating animation comprising a first reciprocating animation of the first ventilation related parameter relative to the first target indication and a second reciprocating animation of the second ventilation related parameter relative to the second target indication, wherein each of said reciprocating animations is in synchronism with a breathing cycle of the patient ventilated by said breathing apparatus and moves from a starting point to an end point in a to-and-fro motion relative said target indications, and wherein said end points provide an indication of whether said first and second ventilation related parameters are below, on point, or are exceeding their respective target indication, wherein the first and second ventilation related parameters are tidal volume per kg body weight (ml/kg) and a pressure, wherein the combined reciprocating animation is provided on the display unit during ventilation of the patient in a pressure support mode, a pressure control mode, a volume support mode, or a volume controlled mode.

17. The system of claim 5, wherein the second reciprocating animation is arranged concentric to the first reciprocating animation.

\*   \*   \*   \*   \*